US012702858B2

(12) United States Patent
Dijkstra

(10) Patent No.: US 12,702,858 B2
(45) Date of Patent: Aug. 11, 2026

(54) DETACHABLE PHOTOTHERAPY DEVICE

(71) Applicant: SHENZHEN KAIYAN MEDICAL EQUIPMENT CO., LTD, Shenzhen (CN)

(72) Inventor: Alain Dijkstra, Amstelveen (NL)

(73) Assignee: Shenzhen Kayan Medical Equipment Co. Ltd, Shenzhen (CN)

( * ) Notice: Subject to any disclaimer, the term of this patent is extended or adjusted under 35 U.S.C. 154(b) by 666 days.

(21) Appl. No.: 18/334,406

(22) Filed: Jun. 14, 2023

(65) Prior Publication Data

US 2024/0269478 A1 Aug. 15, 2024

(30) Foreign Application Priority Data

Feb. 9, 2023 (CN) ......................... 202320160959.6

(51) Int. Cl.
*A61N 5/06* (2006.01)
*A61N 1/04* (2006.01)
*A61N 1/30* (2006.01)

(52) U.S. Cl.
CPC ......... *A61N 5/0616* (2013.01); *A61N 1/0432* (2013.01); *A61N 1/0468* (2013.01); *A61N 1/303* (2013.01); *A61N 2005/0645* (2013.01); *A61N 2005/0652* (2013.01); *A61N 2005/0663* (2013.01)

(58) Field of Classification Search
CPC .......... A61N 2005/0645; A61N 5/0616; A61N 2005/0651; A61N 2005/0652; A61N 5/0613; A61N 5/0624; A61N 2005/0663; A61N 2005/0662; A61N 2005/0658; A61N 2005/0643; A61N 1/0432; A61N 1/0428; A61N 1/0468; A61N 1/30; A61N 1/303
See application file for complete search history.

(56) References Cited

U.S. PATENT DOCUMENTS

| | | | | |
|---|---|---|---|---|
| 8,372,128 | B2 | 2/2013 | Reuben | |
| 2019/0111276 | A1 * | 4/2019 | Tapper | A61N 5/0613 |
| 2023/0390574 | A1 * | 12/2023 | Herbert | A61N 5/0616 |

* cited by examiner

*Primary Examiner* — Jason E Flick
(74) *Attorney, Agent, or Firm* — Willie Jacques; Emanus LLC

(57) ABSTRACT

A detachable phototherapy device includes a substrate layer including a first portion, a second portion, and a bend portion connecting the first portion with the second portion. The detachable phototherapy device further includes a conductive layer printed on a first substrate surface of the substrate layer. The detachable phototherapy device further includes a plurality of light sources electrically coupled to the conductive layer. Further, the detachable phototherapy device includes a first electrode coupled to the first portion, and a second electrode coupled to the second portion. Also, the detachable phototherapy device includes a battery including a first battery terminal, and a second battery terminal. The battery is electrically coupled to one of the first electrode and the second electrode, at one of the first battery terminal and the second battery terminal, respectively, in a non-use state of the detachable phototherapy Device.

17 Claims, 8 Drawing Sheets

DETACHABLE PHOTOTHERAPY DEVICE

TECHNICAL FIELD

The present invention relates generally to the field of Photobiomodulation or light therapy, and more specifically to a detachable and reusable phototherapy device.

BACKGROUND ART

Bandages are applied on wounds to facilitate wound healing. The bandages serve multiple purposes such as keeping severed skin together, applying an antiseptic substance to the wound area, and protecting the wound from environmental elements such as dust, water, and outside micro-organisms such as bacteria and fungi. However, bandages are generally designed for single use and once removed from a wound are thrown away contributing to medical waste generation. Moreover, attachment and removal of the bandages cause some amount of discomfort to a user as the antiseptic portion of the bandage tends to relatively strongly adhere to the skin of the user. Moreover, bandages do little in terms of promoting and expediting wound healing. Therefore, some rather more severe wounds may take a relatively long time and the bandages may need to be replaced several times during that period.

Whereas, electromagnetic radiation, such as visible light is known to have several benefits regarding wound healing. For example, blue light is known to have bactericidal and antiseptic properties. Moreover, red light is known to have replenishing and rejuvenating effects on the skin, as red light promotes the production of collagen and Adenosine Triphosphate (ATP) in skin cells. However, little has been done to combine the properties of electromagnetic radiation with bandages to achieve a combination of benefits available from the bandages and the electromagnetic radiation. Some solutions present in the art combine Organic Light Emitting Diode (OLED) based modules with the bandages to achieve the combined benefits. However, such solutions are complicated in construction and are relatively expensive to design and manufacture.

Therefore, there is a need in the art for phototherapy-based devices that do not suffer from the aforementioned deficiencies.

OBJECTS OF THE INVENTION

Some of the objects of the invention are as follows:

An object of the present invention is to provide a detachable phototherapy device that can be attached to the skin of a user to enhance wound healing and skin regeneration.

Another object of the invention is to provide a detachable phototherapy device that is detachable and can be reused several times.

Another object of the invention is to provide a detachable phototherapy device that is powered using a battery contained within.

Another object of the invention is to provide a detachable phototherapy device that is adapted to emit blue light for its antiseptic and bactericidal properties and red light for its skin regeneration properties.

SUMMARY OF THE INVENTION

According to an aspect of the present invention, there is provided a detachable phototherapy device. The detachable phototherapy device includes a substrate layer including a first substrate surface oriented towards a first direction, a second substrate surface oriented towards a second direction opposite to the first direction, a first portion, a second portion, and a bend portion connecting the first portion with the second portion. The detachable phototherapy device further includes a conductive layer printed on the first substrate surface of the substrate layer, the conductive layer including a first conductor terminal, and a second conductor terminal. Further, the detachable phototherapy device includes a plurality of light sources electrically coupled to the conductive layer, the plurality of light sources configured to emit electromagnetic radiation towards the first direction. The detachable phototherapy device further includes a first electrode coupled to the first portion on a third segment of the second substrate surface, the first electrode electrically coupled to the first conductor terminal. The detachable phototherapy device further includes a second electrode coupled to the second portion on a fourth segment of the second substrate surface, the second electrode electrically coupled to the second conductor terminal. Also, the detachable phototherapy device includes a battery including a first battery terminal and a second battery terminal, the battery electrically coupled to one of the first electrode and the second electrode, at one of the first battery terminal and the second battery terminal, respectively, in a non-use state of the detachable phototherapy device.

In one embodiment of the invention, in a use state of the detachable phototherapy device, the substrate layer is adapted to bend at the bend portion, allowing the battery to be electrically coupled between the first electrode and the second electrode, thereby completing a conductive circuit including the conductive layer, the plurality of light sources, the first electrode, the second electrode, and the battery.

In one embodiment of the invention, the substrate layer is made up of sulphuric acid paper.

In one embodiment of the invention, the plurality of light sources includes a plurality of Light Emitting Diodes (LEDs).

In one embodiment of the invention, all of the plurality of light sources are provided on a first segment of the first surface, provided on the first portion.

In one embodiment of the invention, the plurality of light sources is configured to emit the electromagnetic radiation of wavelength ranges including 620-700 nm and 450-495 nm.

In one embodiment of the invention, the plurality of light sources is configured to emit radiation in visible light and infrared wavelengths of the electromagnetic spectrum.

In one embodiment of the invention, the first electrode is coupled to the first portion, and the second electrode is coupled to the second portion, each using adhesive bonding.

In one embodiment of the invention, the battery is further mechanically coupled to one of the first electrode and the second electrode.

In one embodiment of the invention, the first electrode and the second electrodes are permanent magnets.

In one embodiment of the invention, the battery is electrically coupled to the first electrode at the first battery terminal and the second battery terminal is oriented towards the second direction.

In one embodiment of the invention, the battery is electrically coupled to the second electrode at the second battery terminal and the first battery terminal is oriented towards the second direction.

In one embodiment of the invention, the detachable phototherapy device further includes a sticker including a first sticker surface oriented towards the first direction, and a second sticker surface oriented towards the second direction, the first sticker surface and the second sticker surface provided with adhesive layers. The substrate layer is adapted to be detachably attached to the second sticker surface through adhesive bonding, such that the conductive layer and the plurality of light sources are sandwiched between the first substrate surface of the substrate layer and the second sticker surface of the sticker. Also, the sticker is adapted to be detachably attached to a body portion of a user, along the first sticker surface.

In one embodiment of the invention, the sticker is made up of a non-woven fabric material. Alternatively, the sticker is made of a material that help in absorbing the healing creams, lotions and other ointments to the user skin.

In one embodiment of the invention, the battery is a rechargeable battery.

In one embodiment of the invention, the detachable phototherapy device further includes at least one first electrode attached to the conductive layer and electrically coupled to the first conductor terminal, and at least one second electrode attached to the conductive layer and electrically coupled to the second conductor terminal.

In one embodiment of the invention, the at least one first electrode and the at least one second electrode are made up of electrically conductive silicone material.

In one embodiment of the invention, the at least one first electrode and the at least one second electrode are configured to provide iontophoresis therapy to a portion of skin of a user.

In one embodiment of the invention, the at least one first electrode and the at least one second electrode are configured to provide therapies including Electronic Muscle Stimulation (EMS), and Transcutaneous Electrical Nerve Stimulation (TENS).

In an alternative embodiment, the device further comprises, a control unit, a timer and a mode controller.

BRIEF DESCRIPTION OF THE ACCOMPANYING DRAWINGS

The accompanying drawings illustrate the best mode for carrying out the invention as presently contemplated and set forth hereinafter. The present invention may be more clearly understood from a consideration of the following detailed description of the preferred embodiments taken in conjunction with the accompanying drawings wherein like reference letters and numerals indicate the corresponding parts in various figures in the accompanying drawings, and in which.

DETAILED DESCRIPTION

Figure 1A:
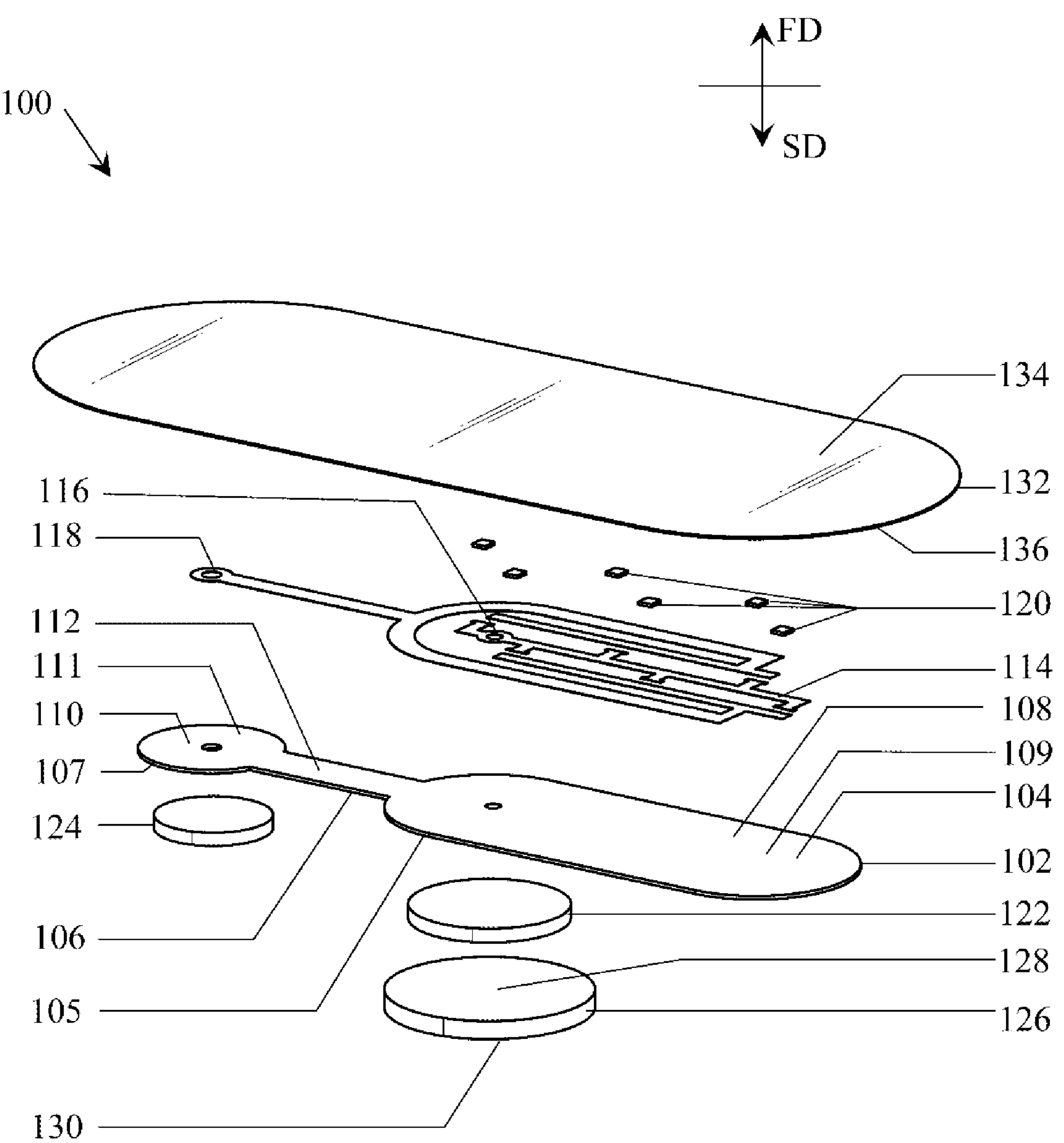
FIG. 1A illustrates an exploded view of a detachable phototherapy device, in accordance with an embodiment of the present invention.

Embodiments of the present invention disclosure will be described more fully hereinafter with reference to the accompanying drawings in which like numerals represent like elements throughout the figures, and in which example embodiments are shown.

The detailed description and the accompanying drawings illustrate the specific exemplary embodiments by which the disclosure may be practiced. These embodiments are described in detail to enable those skilled in the art to practice the invention illustrated in the disclosure. It is to be understood that other embodiments may be utilized, and other changes may be made, without departing from the spirit or scope of the present disclosure. The following detailed description is therefore not to be taken in a limiting sense, and the scope of the present invention disclosure is defined by the appended claims. Embodiments of the claims may, however, be embodied in many different forms and should not be construed as limited to the embodiments set forth herein.

In the context of this specification, terms like “light”, “radiation”, “irradiation”, “emission” and “illumination”, etc. refer to electromagnetic radiation in wavelength ranges varying from the visible light wavelengths (380-700 nm) to Infrared (IR) wavelengths (780 nm-1 mm), wherein the range is inclusive of visible light and IR wavelengths. The IR radiation may also be categorized into several categories according to respective wavelength ranges which are again envisaged to be within the scope of this invention. A commonly used subdivision scheme for IR radiation includes Near IR (0.75-1.4 μm), Short-Wavelength IR (1.4-3 μm), Mid-Wavelength IR (3-8 μm), Long-Wavelength IR (8-15 μm) and Far IR (15-1000 μm).

In the context of the specification, “Light Emitting Diodes (LEDs)” are envisaged to be semiconductor devices that emit electromagnetic radiation when current is applied through them. LEDs are characterized by their superior power efficiencies, smaller sizes, rapidity in switching, physical robustness, and longevity when compared with incandescent or fluorescent lamps. In that regard, the plurality of LEDs may be through-hole type LEDs (generally used to produce electromagnetic radiations of red, green, yellow, blue and white colors), Surface Mount LEDs, Bi-color LEDs, Pulse Width Modulated RGB (Red-Green-Blue) LEDs, and high-power LEDs, etc.

Materials used in the construction of LEDs may vary from one embodiment to another depending upon the frequency of radiation required. Different frequencies can be obtained from LEDs made from pure or doped semiconductor materials. Commonly used semiconductor materials include nitrides of Silicon, Gallium, Aluminum, and Boron, and Zinc Selenide, etc. in pure form or doped with elements such as Aluminum and Indium, etc. For example, red and amber colors are produced from Aluminum Indium Gallium Phosphide (AlGalnP) based compositions, while blue, green, and cyan use Indium Gallium Nitride based compositions. White light may be produced by mixing red, green, and blue lights in equal proportions, while varying proportions may be used for generating a wider color gamut. White and other colored lightings may also be produced using phosphor coatings such as Yttrium Aluminum Garnet (YAG) in combination with a blue LED to generate white light and Magnesium doped potassium fluorosilicate in combination with blue LED to generate red light. Additionally, near Ultraviolet (UV) LEDs may be combined with europium-based phosphors to generate red and blue lights, and copper and zinc doped zinc sulfide-based phosphor to generate green light.

In addition to conventional mineral-based LEDs, one or more LEDs may also be provided on an Organic LED (OLED) based flexible panel or an inorganic LED-based flexible panel. Such OLED panels may be generated by depositing organic semiconducting materials over Thin Film Transistor (TFT) based substrates. Further, discussion on generation of OLED panels can be found in Bardsley, J. N (2004), "International OLED Technology Roadmap", IEEE Journal of Selected Topics in Quantum Electronics, Vol. 10, No. 1, that is included herein in its entirety, by reference. An exemplary description of flexible inorganic light-emitting diode strips can be found in granted U.S. Pat. No. 7,476,557 B2, titled "Roll-to-roll fabricated light sheet and encapsulated semiconductor circuit devices", which is included herein in its entirety, by reference.

In several embodiments, the one or more LEDs may also be micro-LEDs described through U.S. Pat. Nos. 8,809,126 B2, 8,846,457 B2, 8,852,467 B2, 8,415,879 B2, 8,877,101 B2, 9,018,833 B2 and their respective family members, assigned to Nth Degree Technologies Worldwide Inc., which are included herein by reference, in their entirety. The one or more LEDs, in that regard, may be provided as a printable composition of the micro-LEDs, printed on a substrate.

In the context of the specification, the term "lontophoresis" refers to application of direct current to the epidermis of a patient. lontophoresis includes the application of galvanic current on the positive polarity. During an iontophoresis treatment, a product that has an acidic pH and is water-soluble can be used. Gels, serums, or even a mask can be applied all over the area to be treated.

It is envisaged that a detachable phototherapy device be provided that can be used as a bandage for promoting wound healing and skin regeneration. The detachable phototherapy device may include a conductive layer printed and/or deposited on a substrate layer, and several light sources, such as, but not limited to, Light Emitting Diodes (LEDs), electrically coupled to the conductive layer. The substrate layer may be made up of sulphuric acid paper. Further, the substrate layer may include a first portion on which the several LEDS, one of two electrodes, and a battery may be provided. Further, the substrate layer may include a second portion on which a second electrode of the two electrodes may be provided.

The first and the second portion may be connected through a bend portion. The bend portion may be adapted to bend, in a manner that the second portion is moved towards the first portion to position the battery between the two electrodes, thereby completing an electrical power circuit for the several light sources. The battery may be a rechargeable battery. Further, electrodes made from a conductive material, such as conductive silicone, may be attached to the conductive layer to provide iontophoresis to a portion of skin of a user. It is also envisaged that the substrate layer may be detachably attached to a sticker made out of a non-woven fabric material, through adhesive bonding. The sticker with the substrate layer detachably attached therewith and including the several sources powered by the battery, therebetween, may then be applied to a wounded portion of the skin of the user. Referring to the drawings, the present invention will now be discussed in more detail.

FIG. 1A illustrates an exploded view of a detachable phototherapy device 100 (hereinafter referred to as "the device 100"), in accordance with an embodiment of the present invention. The device 100 includes a substrate layer 102. In several embodiments of the invention, the substrate layer 102 is made up of sulphuric acid paper. The sulphuric acid paper offers several advantages, such as, the sulphuric acid paper is characterized by high density, stability, heat resistance, grease resistance, water resistance, no loose fibers as well as low surface energy, thereby imparting good non-stick or release properties to the substrate layer 102 and also helps in wound healing. The aforementioned properties of the sulphuric acid paper make the sulphuric acid paper ideal for bandages.

The substrate layer 102 includes a first substrate surface 104 oriented towards a first direction (FD). The first direction (FD) may be in a direction of application of the device 100 on a skin of a user. The substrate layer 102 further includes a second substrate surface 106 oriented towards a second direction (SD). The second direction (SD) is envisaged to be opposite to the first direction (FD). Further, the substrate layer 102 includes a first portion 108. In one embodiment of the invention, the first portion 108 is envisaged to be longitudinal in shape, with a first predetermined thickness. The first portion 108 includes a first segment 109 of the first substrate surface 104. Further, the first portion 108 includes a third segment 105 of the second substrate surface 106.

The substrate layer 102 further includes a second portion 110. In one embodiment of the invention, the second portion 110 is envisaged to be circular in shape, with a second predetermined thickness. In several embodiments of the invention, the first predetermined thickness is equal to the second predetermined thickness. The second portion 110 includes a second segment 111 of the first substrate surface 104, and a fourth segment 107 of the second substrate surface 106. A bend portion 112 connects the first portion 108 with the second portion 110. In several embodiments of the invention, the bend portion 112 is rectangular in shape. Moreover, in several embodiments of the invention, a width of the bend portion 112 is smaller than respective widths of the first portion 108 and the second portion 110, making the bend portion 112 more slender and easier to bend with respect to the first portion 108 and the second portion 110.

A conductive layer 114 has been printed (or deposited) on the first substrate surface 104 of the substrate layer 102. The conductive layer 114 may be made up of an electrically conductive material such as, but not limited to, copper, aluminum, etc. The conductive layer 114 may be printed by depositing the electrically conductive material onto the first substrate surface 104 of the substrate layer 102. The conductive layer 114 includes a first conductor terminal 116 and a second conductor terminal 118. In one embodiment of the invention, the first conductor terminal 116 is located on the first segment 109 of the first substrate surface 104, and the second conductor terminal 118 is located on the second segment 111 of the first substrate surface 104.

Further, the device 100 includes a plurality of light sources 120 electrically coupled to the conductive layer 114. In one embodiment of the invention, the plurality of light sources 120 includes a plurality of Light Emitting Diodes (LEDs). In several alternate embodiments, the plurality of light sources 120 may also include incandescent light sources, or lasers, without departing from the scope of the invention. In one embodiment of the invention, all of the plurality of light sources 120 may be provided on the first segment 109 of the first substrate surface 104.

The plurality of light sources 120 are configured to emit electromagnetic radiation towards the first direction (FD). In that regard, the plurality of light sources 120 may be configured to emit the electromagnetic radiation of wavelength ranges including 620-700 nm (red light) and 450-495 nm (blue light). The red light is known to promote skin repair, regeneration and rejuvenation by enhancing the production of collagen and Adenosine Triphosphate (ATP). Further, the blue light is known for its bactericidal and antiseptic properties. Therefore, both the red light and the blue light would expedite the process of wound healing.

Further, the device 100 includes a first electrode 122 and a second electrode 124. The first electrode 122 is coupled to the first portion 108 on the third segment 105 of the second substrate surface 106. The first electrode 122 may be coupled to the first portion 108 using adhesive bonding. The second electrode 124 is coupled to the second portion 110 on the fourth segment 107 of the second substrate surface 106. The second electrode 124 may be coupled to the second portion 110 also using the adhesive bonding. Further, the first electrode 122 is electrically coupled to the first conductor terminal 116. Also, the second electrode 124 is electrically coupled to the second conductor terminal 118. In that regard, the first portion 108 and the second portion 110 may include holes through which electrical conductors may pass, and connect the first electrode 122 with the first conductor terminal 116 and the second electrode 124 with the second conductor terminal 118.

The device 100 further includes a battery 126. The battery 126 includes a first battery terminal 128 and a second battery terminal 130. In one embodiment of the invention, the first battery terminal 128 may be a positive terminal and the second battery terminal 130 may be a negative terminal. In an alternate embodiment, the first battery terminal 128 may be the negative terminal and the second battery terminal 130 may be the positive terminal. In one embodiment of the invention, in a non-use state of the device 100, the battery 126 is electrically coupled to the first electrode 122 through the first battery terminal 128, and the second battery terminal 130 is oriented towards the second direction (SD). In another embodiment of the invention, in the non-use state of the device 100, the battery 126 may be electrically coupled to the second electrode 124 through the second battery terminal 130, and the first battery terminal 128 may be oriented towards the second direction (SD).

In addition to the electrical coupling, the battery 126 may also be mechanically coupled to either one of the substrate layer 102, the first electrode 122, and the second electrode 124. The mechanical coupling with the substrate layer 102 may be achieved by attaching the battery 126 adhesively to one of the first substrate surface 104 and the second substrate surface 106. The mechanical coupling with the first electrode 122 or the second electrode 124 may be achieved through snap-fit fastening, clip-based fastening, or magnetic fastening. In that regard, in several embodiments of the invention, the first electrode 122 and the second electrode 124 may be permanent magnets. In several embodiments of the invention, the battery 126 may be a rechargeable battery. For example, the battery 126 may be a Nickel-Metal-Hydride battery, Lithium-ion battery, or a Lithium polymer battery.

In several embodiments of the invention, the device 100 further includes a sticker 132. The sticker 132 further includes a first sticker surface 134 oriented towards the first direction (FD), and a second sticker surface 136 oriented towards the second direction (SD). The first sticker surface 134 and the second sticker surface 136 may be provided with adhesive layers. In several embodiments of the invention, the adhesives provided on the first sticker surface 134 and the second sticker surface 136 may be identical. In several alternate embodiments, the adhesives provided on the first sticker surface 134 and the second sticker surface 136 may be non-identical. The adhesive layer on the first sticker surface 134 may be provided with a liner strip over the adhesive layer, in the non-use state of the device 100. The adhesive layer of the second sticker surface 136 may be used to bond the first substrate surface 104. The conductive layer 114 and the plurality of light sources 120 may be disposed between the substrate layer 102 and the sticker 132.

In other words, the substrate layer 102 is adapted to be detachably attached to the second sticker surface 136 through adhesive bonding, such that the conductive layer 114 and the plurality of light sources 120 are sandwiched between the first substrate surface 104 of the substrate layer 102 and the second sticker surface 136 of the sticker 132. Further, the sticker 132 is adapted to be detachably attached to a body portion of a user, along the first sticker surface 134. The sticker 134 may be attached to the body portion of the user, after removal of the liner strip from over the adhesive layer of the first sticker surface 134. In several embodiments of the invention, the sticker 132 may be made up of a non-woven fabric material. The non-woven fabric materials are characterized by their ability to absorb moisture, resist bacterial infestation, and repel liquids, resilience, softness, sterility, strength, cushioning, thermal insulation, and washability.

Figure 1B:
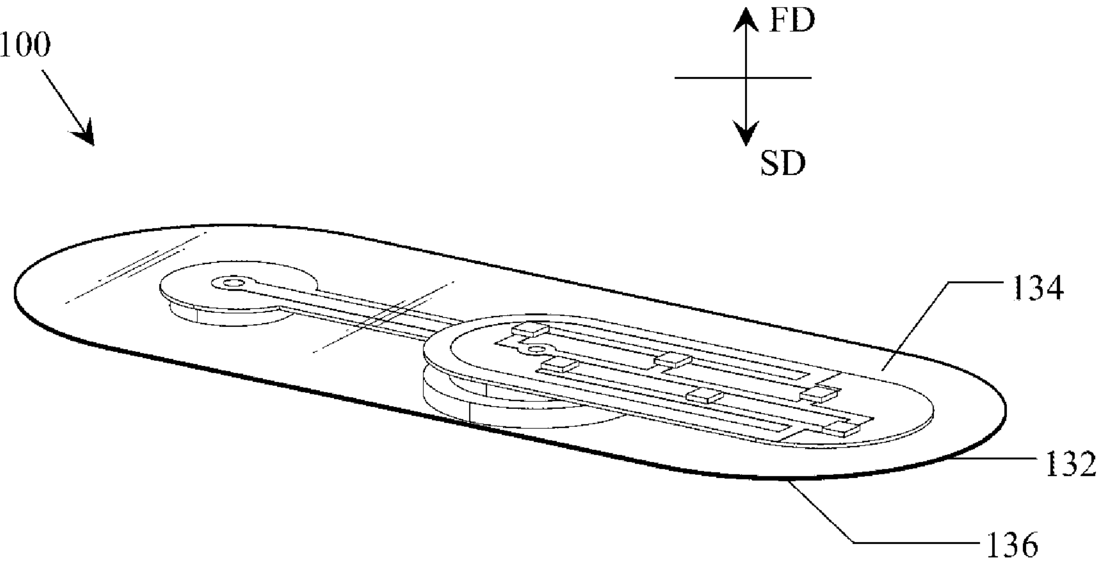
FIG. 1B illustrates a top perspective view of the detachable phototherapy device of FIG. 1A.
Figure 1C:
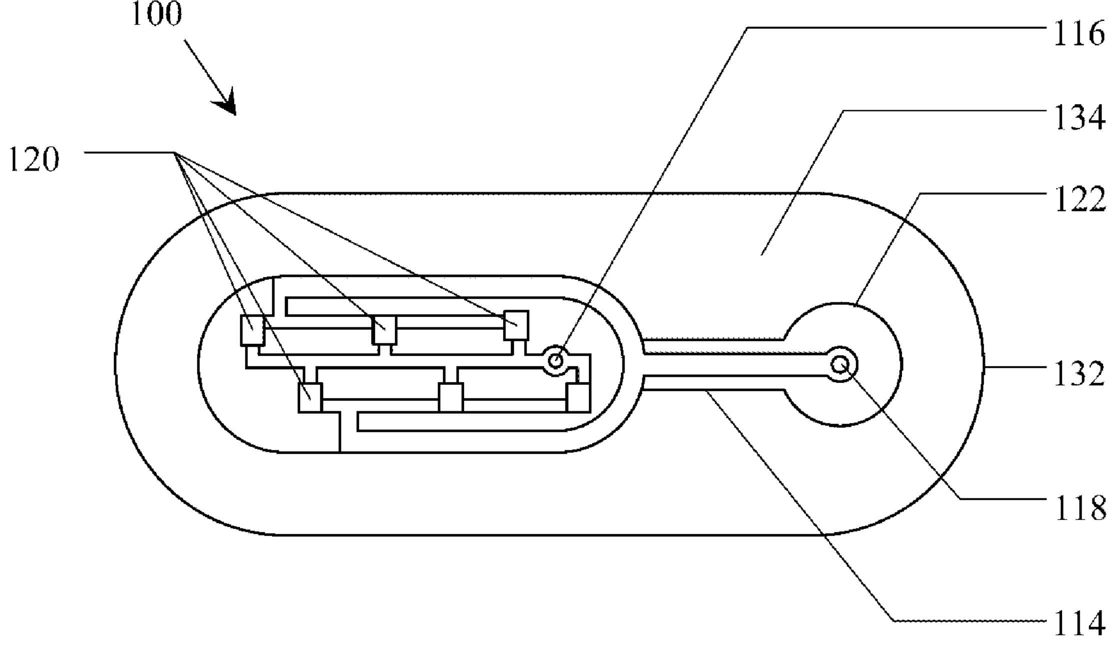
FIG. 1C illustrates a bottom view of the detachable phototherapy device of FIG. 1A.

FIG. 1B illustrates a top perspective view of the device 100 of FIG. 1A. FIG. 1C illustrates a bottom view of the device 100 of FIG. 1A. FIGS. 1B and 1C illustrate the sticker 132 with the first sticker surface 134 and the second sticker surface 136. Further illustrated are the conductive layer 114, the plurality of light sources 120, the first conductor terminal 116, the second conductor terminal 118, and the first electrode 122.

Figure 2:
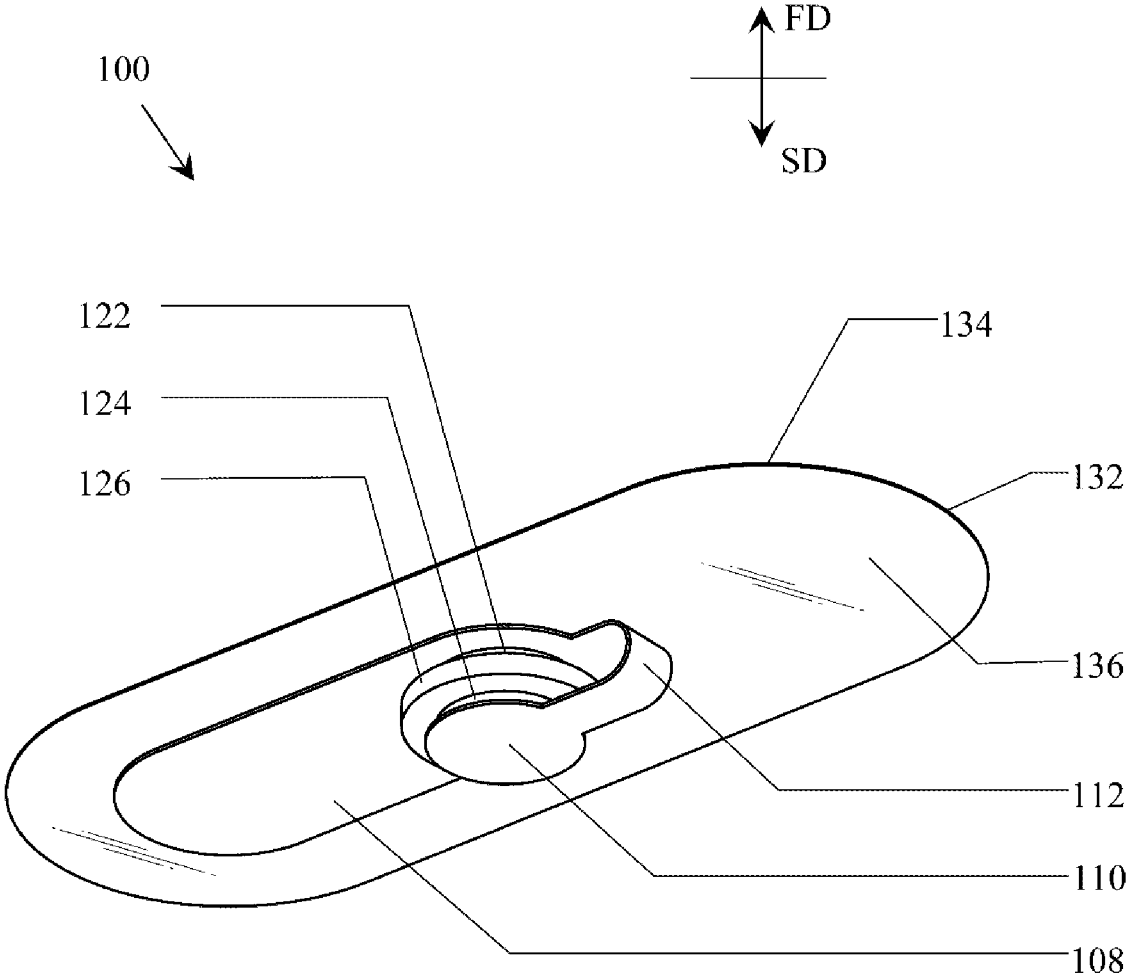
FIG. 2 illustrates a bottom perspective view of the detachable phototherapy device in a use state, in accordance with an embodiment of the present invention.

FIG. 2 illustrates a bottom perspective view of the device 100 in a use state, in accordance with an embodiment of the present invention. In the use state, the substrate layer 102 is adapted to bend at the bend portion 112, allowing the battery 126 to be electrically coupled between the first electrode 122 and the second electrode 124. In that regard, the first battery terminal 128 is electrically coupled to the first electrode 122, and the second battery terminal 130 is electrically coupled to the second electrode 124. As a result, a conductive circuit including the conductive layer 114, the plurality of light sources 120, the first electrode 122, the second electrode 124, and the battery 126 is completed.

Figure 3:
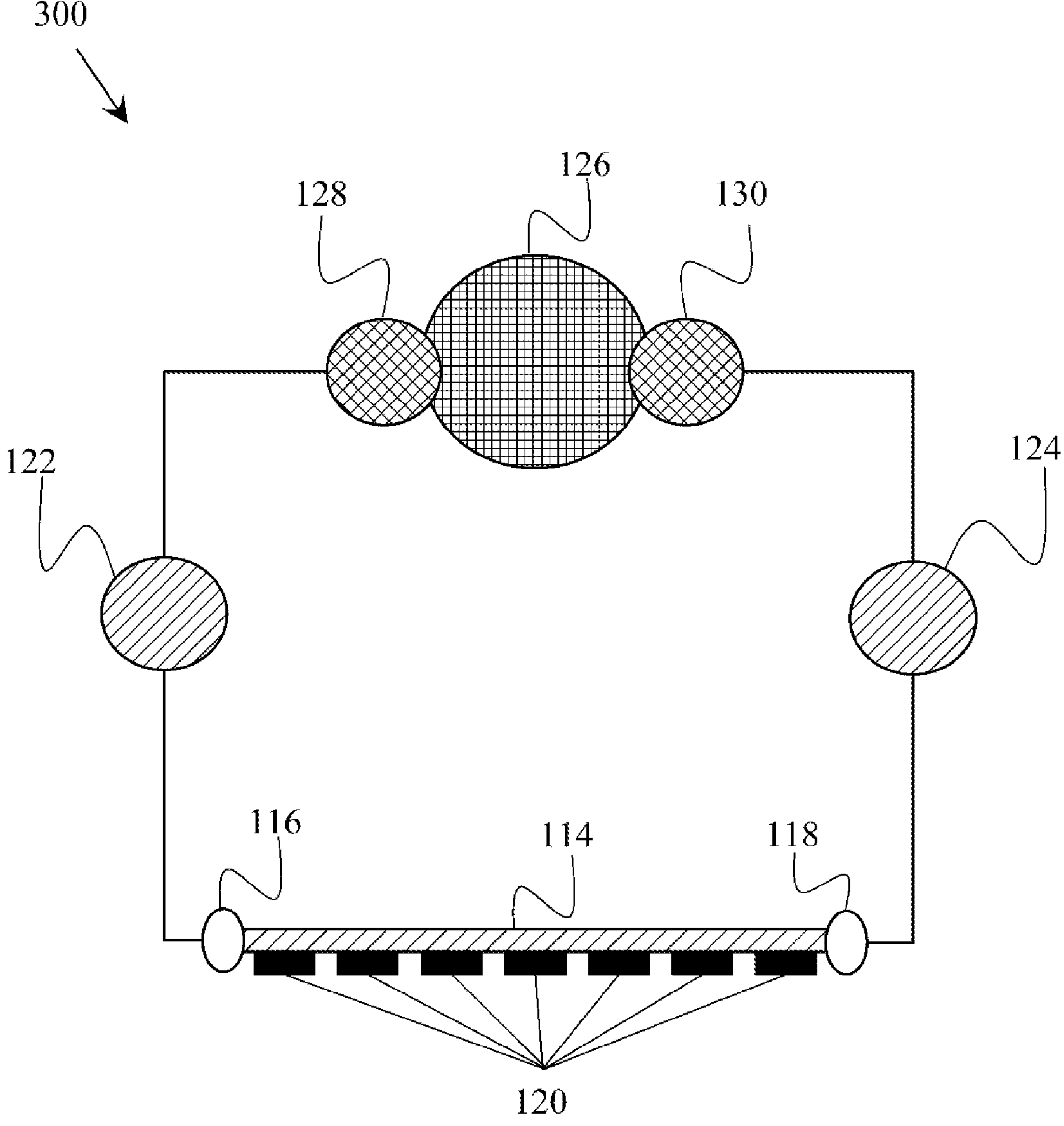
FIG. 3 illustrates a logical circuit diagram of the detachable phototherapy device in the use state, in accordance with an embodiment of the present invention.

FIG. 3 illustrates a logical circuit diagram 300 of the device 100 in the use state, in accordance with an embodiment of the present invention. As illustrated in FIG. 3, the battery 120 includes the first battery terminal 128 and the second battery terminal 130. The first battery terminal 128 is electrically coupled to the first electrode 122, and the second battery terminal 130 is electrically coupled to the second electrode 124. The plurality of light sources 120 have been electrically attached to the conductive layer 114. The conductive layer 114 includes the first conductor terminal 116 and the second conductor terminal 118. The first conductor terminal 116 is electrically coupled to the first electrode 122, and the second conductor terminal 118 is electrically coupled to the second electrode 124. As a result, a circuit is completed allowing the battery 126 to power the plurality of light sources 120.

Figure 4A:
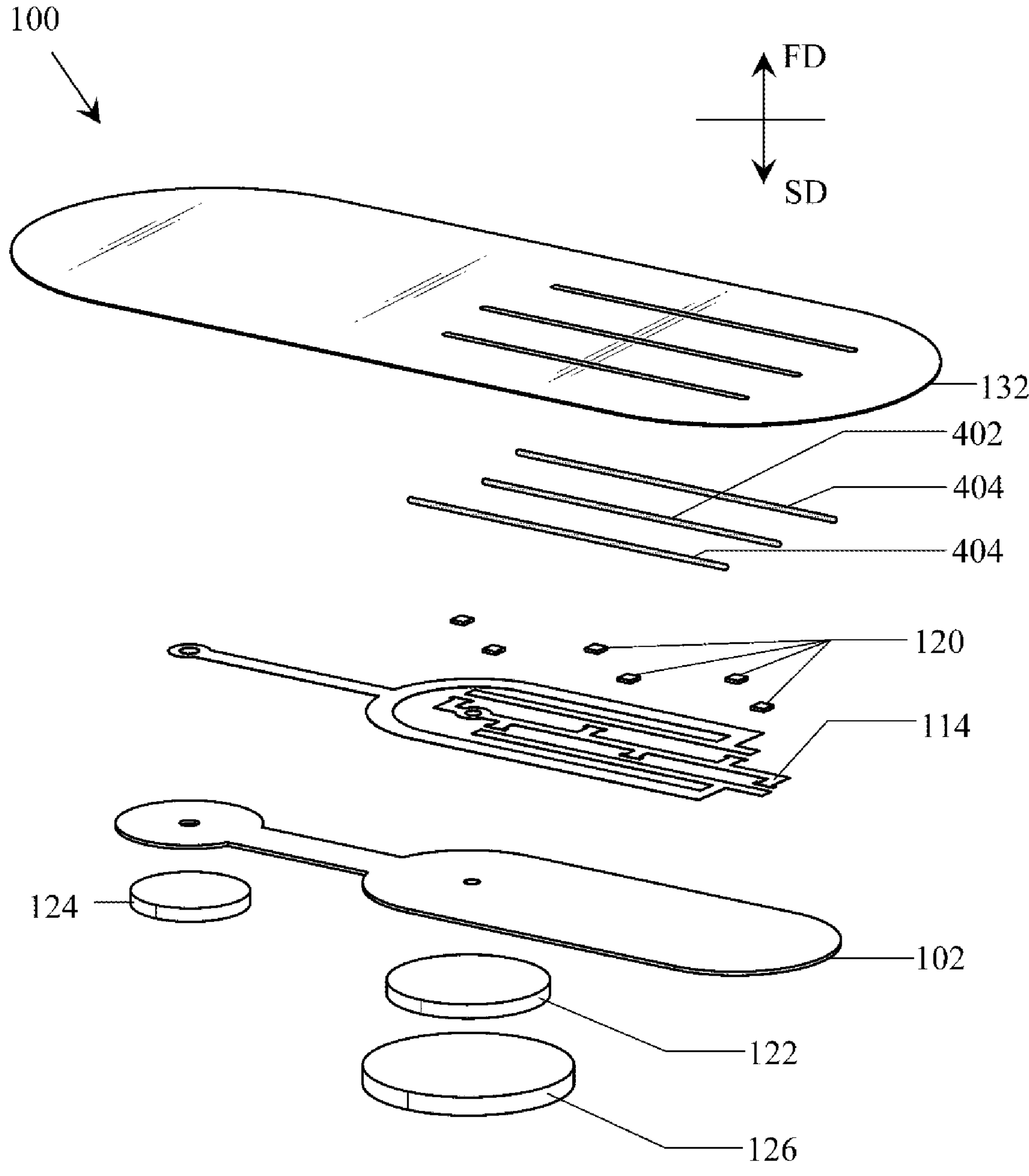
FIG. 4A illustrates an exploded view of the detachable phototherapy device, in accordance with another embodiment of the present invention.
Figure 4B:
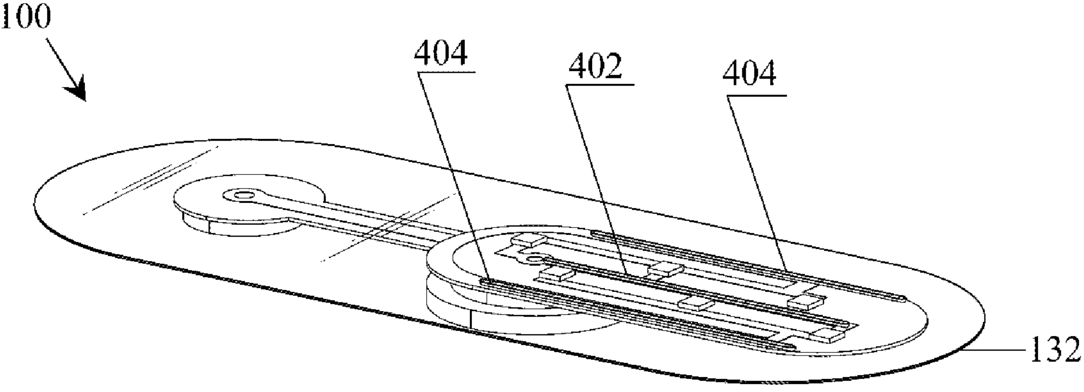
FIG. 4B illustrates a top perspective view of the detachable phototherapy device of FIG. 4A.
Figure 4C:
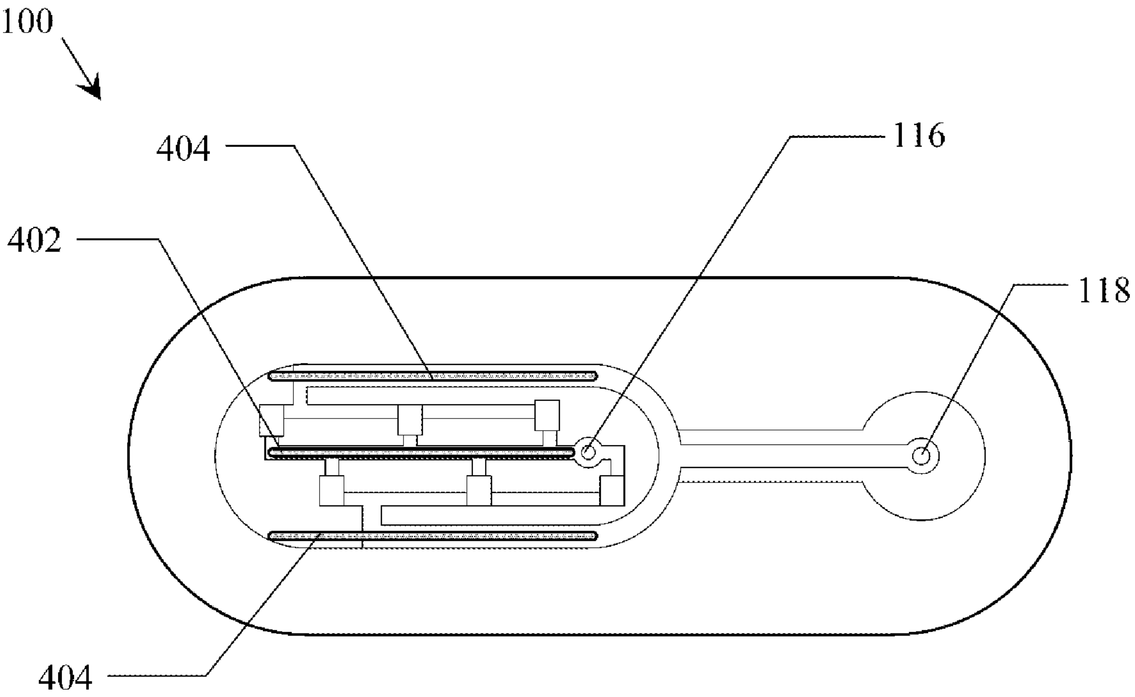
FIG. 4C illustrates a bottom view of the detachable phototherapy device of FIG. 4A.

FIG. 4A illustrates an exploded view of the detachable phototherapy device 100, in accordance with another embodiment of the present invention. FIG. 4B illustrates a top perspective view of the detachable phototherapy device 100 of FIG. 4A. FIG. 4C illustrates a bottom view of the detachable phototherapy device 100 of FIG. 4A. Referring to FIGS. 4A, 4B, and 4C, the detachable phototherapy device 100 further includes at least one first electrode 402 attached to the conductive layer 114 and electrically coupled to the first conductor terminal 116. Further, the detachable phototherapy device 100 includes at least one second electrode 404 attached to the conductive layer 114 and electrically coupled to the second conductor terminal 118. The at least one first electrode 402 and the at least one second electrode 404 are envisaged to be made up of electrically conductive materials, so that they are able to be charged as per the polarity of the first conductor terminal 116 and the second conductor terminal 118, respectively. In that regard, one of the at least one first electrode 402 and the at least one second electrode 404 will be positively charged and the other would be negatively charged. In several embodiments of the invention, the at least one first electrode 402 and the at least one second electrode 404 are made up of electrically conductive silicone material. The electrically conductive silicone material is typically made from impregnating silicone material with carbon. As a consequence, the at least one first electrode 402 and the at least one second electrode 404 are configured to provide iontophoresis therapy to a portion of skin of a user.

lontophoresis involves active transdermal drug delivery involving delivery of drug ions through the skin using low level electric current. When Direct Current (DC) is applied to an ionized drug solution, ions that have same charge as the current are repelled by the current and delivered through the skin. For example, the ionized drug solution may be applied to a hand of the user and the device 100 may be attached to the area where the ionized drug solution has been applied. The DC current is applied through the conductive layer 114 and the at least one first electrode 402 and the at least one second electrode 404. The ions in the drug solution are repelled and absorbed through the hand of the user and provide pain relief to the user. lontophoresis can be used with water soluble ionic medications to treat acute tendonitis, pain associated with calcific deposits, and provide dermal anesthesia. Iontophoresis has several advantages over alternatives to injections and oral medications. lontophoresis is virtually painless and is non-invasive minimizing the risk of infection and tissue necrosis and tendon rupture.

Figure 5:
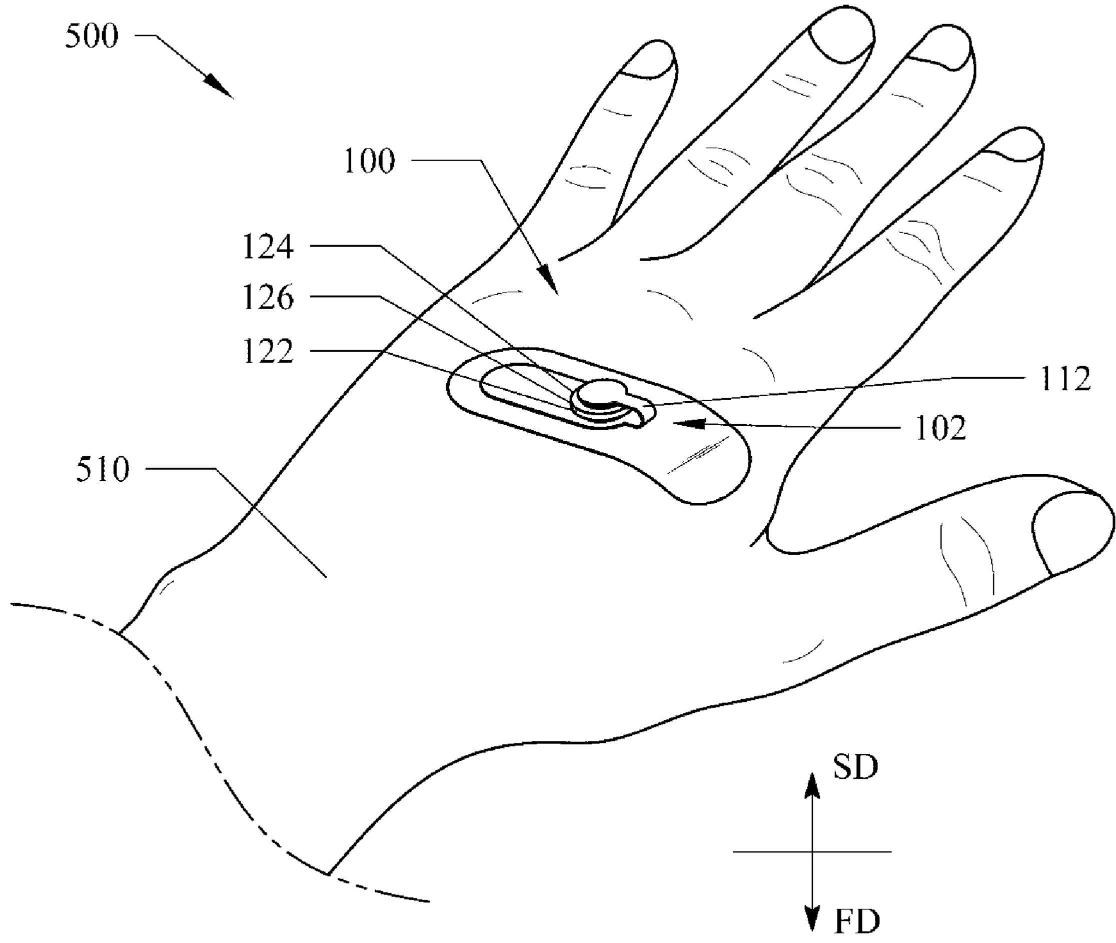
FIG. 5 illustrates a use case scenario of the detachable phototherapy device, with the detachable phototherapy device applied on the skin of a user, in accordance with an embodiment of the present invention.

FIG. 5 illustrates a use case scenario 500 of the device 100, with the device 100 applied on the skin of a user 510, in accordance with an embodiment of the present invention. In the use case scenario, the liner strip on the adhesive layer of the first sticker surface 134 may be removed, and the first sticker surface 134 may be adhesively applied to an affected area on the skin of the user 400. The substrate layer 102 may be bent at the bend portion 112 electrically coupling the battery 126 between the first electrode 122 and the second electrode 124. The circuit may therefore be completed and the plurality of light sources 120 would begin to emit the electromagnetic radiation in red and blue visible light frequencies to provide bactericidal and anti-septic effect and promote skin regeneration and repair in the affected area of the skin of the user. Further, in several embodiments, the at least one first electrode 402 and the at least one second electrode 404 would be able to provide iontophoresis therapy to a portion of the skin of the user 510, where the device 100 has been applied. After use, the substrate layer 102 with the conductive layer 114, the plurality of light sources 120, the first electrode 122, the second electrode 124, and the battery 126 may be removed from the sticker 132 and adhesive bonded to another new sticker. This allows the device 100 to be used several times over with only the sticker 132 having to be discarded.

Figure 6:
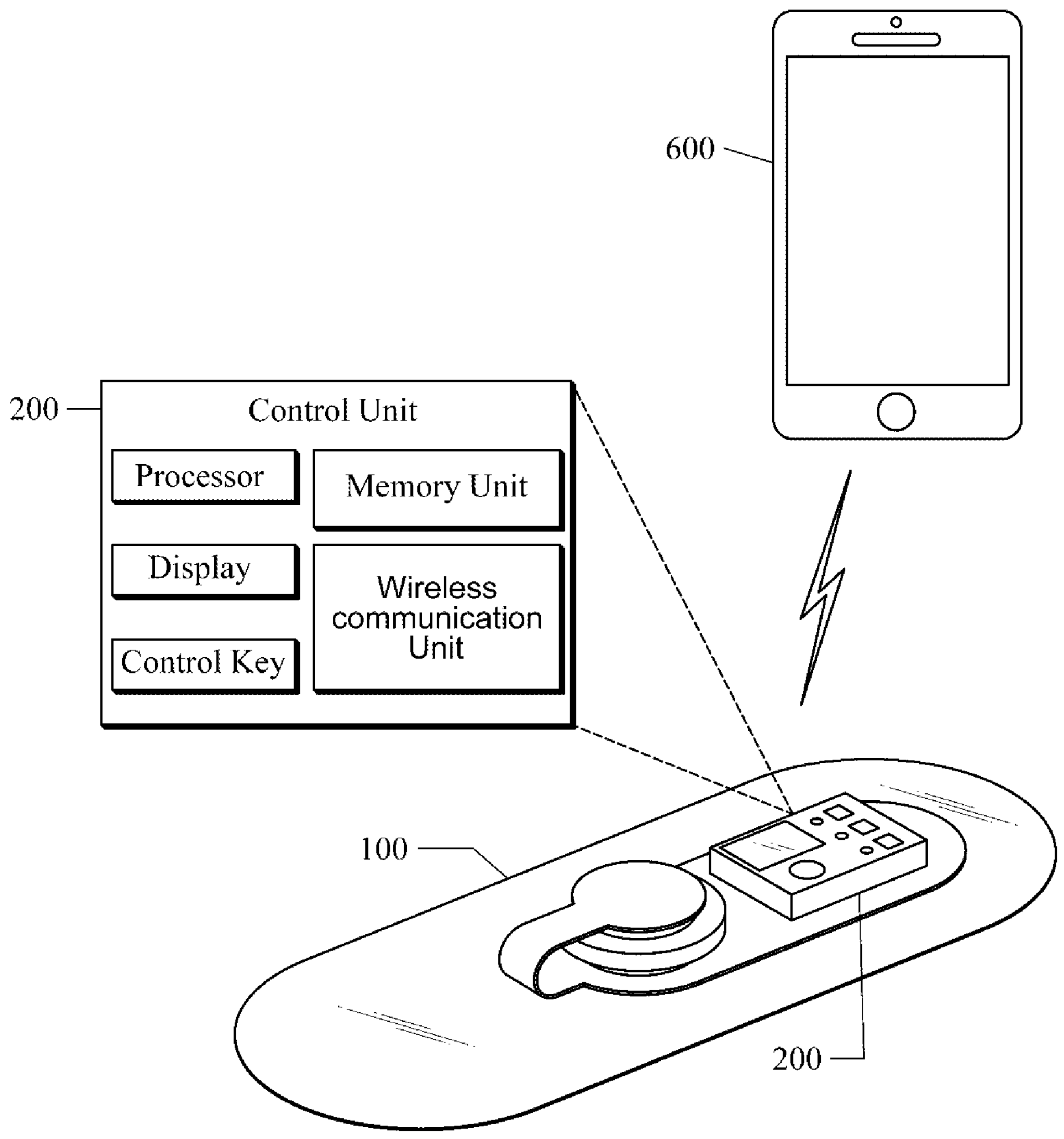
FIG. 6 is an alternate embodiment showing the device with a control unit communicating to an external communication device.

FIG. 6 shows an alternative embodiment, the device 100 includes a control unit 200 configured to connect with an external communication device 600 and receive an input from the external communication device 600. The control unit includes a processor, a memory unit control keys and a display. The memory unit includes machine-readable instructions for the processor to execute. The communication with the external communication device 600 is routed through the display and control keys via wireless communication unit. The control unit 200 is configured to connect with the external communication device 600 and receive an input. The device 100 allows a user to provide input through the control keys and the display unit to switching between different therapies, such as TENS, EMS, iontophoresis, switching between continuous and pulse mode of operation of the LEDs or modification of emission characteristics of the plurality of LEDs such as wavelength of the irradiation, setting time duration of different therapies using a timer.

The invention as described above offers several advantages. For instance, the detachable phototherapy device is very simple in design and construction. Further, the detachable phototherapy device uses commonly available materials. The simplicity in design and construction, and the use of commonly available materials allow the detachable phototherapy device to be mass-produced with minimal capital expenditure, and to be made available in the market at significantly lower prices. Also, the detachable phototherapy device can be reused several times and is, therefore, cost-effective for the end user and minimizes waste generation.

Various modifications to these embodiments are apparent to those skilled in the art, from the description and the accompanying drawings. The principles associated with the various embodiments described herein may be applied to other embodiments. Therefore, the description is not intended to be limited to the embodiments shown along with the accompanying drawings but is to be providing the broadest scope consistent with the principles and the novel and inventive features disclosed or suggested herein. Accordingly, the invention is anticipated to hold on to all other such alternatives, modifications, and variations that fall within the scope of the present invention and appended claims

The invention claimed is:

1. A detachable phototherapy device, the detachable phototherapy device comprising:

a substrate layer comprising a first substrate surface oriented towards a first direction, a second substrate surface oriented towards a second direction opposite to the first direction, a first portion, a second portion, and a bend portion connecting the first portion with the second portion;

a conductive layer printed on the first substrate surface of the substrate layer, the conductive layer comprising a first conductor terminal and a second conductor terminal;

a plurality of light sources electrically coupled to the conductive layer, the plurality of light sources configured to emit electromagnetic radiation towards the first direction;

a first electrode coupled to the first portion on a third segment of the second substrate surface, the first electrode electrically coupled to the first conductor terminal;

a second electrode coupled to the second portion on a fourth segment of the second substrate surface, the second electrode electrically coupled to the second conductor terminal; and a battery comprising a first battery terminal and a second battery terminal, the battery electrically coupled to one of the first electrode and the second electrode, at one of the first battery terminal and the second battery terminal, respectively, in a non-use state of the detachable phototherapy device.

2. The detachable phototherapy device as claimed in claim 1, wherein, in a use state of the detachable phototherapy device, the substrate layer is adapted to bend at the bend portion, allowing the battery to be electrically coupled between the first electrode and the second electrode, thereby completing a conductive circuit including the conductive layer, the plurality of light sources, the first electrode, the second electrode, and the battery.

3. The detachable phototherapy device as claimed in claim 1, wherein the substrate layer is made up of sulphuric acid paper.

4. The detachable phototherapy device as claimed in claim 1, wherein the plurality of light sources comprises a plurality of Light Emitting Diodes (LEDs).

5. The detachable phototherapy device as claimed in claim 1, wherein all of the plurality of light sources are provided on a first segment of the first surface, provided on the first portion.

6. The detachable phototherapy device as claimed in claim 1, wherein the plurality of light sources are configured to emit the electromagnetic radiation of wavelength ranges including 620-700 nm and 450-495 nm.

7. The detachable phototherapy device as claimed in claim 1, wherein the first electrode is coupled to the first portion and the second electrode is coupled to the second portion, each using adhesive bonding.

8. The detachable phototherapy device as claimed in claim 1, wherein the battery is further mechanically coupled to one of the first electrode and the second electrode.

9. The detachable phototherapy device as claimed in claim 8, wherein the first electrode and the second electrodes are permanent magnets.

10. The detachable phototherapy device as claimed in claim 1, wherein the battery is electrically coupled to the first electrode at the first battery terminal and the second battery terminal is oriented towards the second direction.

11. The detachable phototherapy device as claimed in claim 1, wherein the battery is electrically coupled to the second electrode at the second battery terminal and the first battery terminal is oriented towards the second direction.

12. The detachable phototherapy device as claimed in claim 1, further comprising:

a sticker comprising a first sticker surface oriented towards the first direction, and a second sticker surface oriented towards the second direction, the first sticker surface and the second sticker surface provided with adhesive layers, wherein the substrate layer is adapted to be detachably attached to the second sticker surface through adhesive bonding, such that the conductive layer and the plurality of light sources are sandwiched between the first substrate surface of the substrate layer and the second sticker surface of the sticker, and wherein the sticker is adapted to be detachably attached to a body portion of a user, along the first sticker surface.

13. The detachable phototherapy device as claimed in claim 12, wherein the sticker is made up of a non-woven fabric material.

14. The detachable phototherapy device as claimed in claim 1, wherein the battery is a rechargeable battery.

15. The detachable phototherapy device as claimed in claim 1, further comprising:

at least one first electrode attached to the conductive layer and electrically coupled to the first conductor terminal; and at least one second electrode attached to the conductive layer and electrically coupled to the second conductor terminal.

16. The detachable phototherapy device as claimed in claim 15, wherein the at least one first electrode and the at least one second electrode are made up of electrically conductive silicone material.

17. The detachable phototherapy device as claimed in claim 15, wherein the at least one first electrode and the at least one second electrode are configured to provide iontophoresis therapy to a portion of skin of a user.

* * * * *